US00PP33620P2

(12) United States Plant Patent
Gerits

(10) Patent No.: US PP33,620 P2
(45) Date of Patent: Nov. 2, 2021

(54) ***ECHINACEA* PLANT NAMED 'ES18-20-01'**

(50) Latin Name: *Echinacea purpurea*
Varietal Denomination: ES18-20-01

(71) Applicant: Werner Gerits, Kempen (DE)

(72) Inventor: Werner Gerits, Kempen (DE)

(73) Assignee: Perennial Green GMBH

( * ) Notice: Subject to any disclaimer, the term of this patent is extended or adjusted under 35 U.S.C. 154(b) by 0 days.

(21) Appl. No.: 17/131,126

(22) Filed: Dec. 22, 2020

(51) Int. Cl.
*A01H 5/02* (2018.01)
*A01H 6/14* (2018.01)

(52) U.S. Cl.
USPC ..... Plt./428
CPC ..... *A01H 6/1448* (2018.05)

(58) Field of Classification Search
USPC ..... Plt./428
CPC ..... A01H 6/1448; A01H 5/02
See application file for complete search history.

*Primary Examiner* — Keith O. Robinson
(74) *Attorney, Agent, or Firm* — Cassandra Bright

(57) ABSTRACT

A new and distinct plant of *Echinacea purpurea* named 'ES18-20-01' is disclosed, characterized by ray florets typically colored Orange-Red 34B, heavily overlayed with Red 46B and a dark greyed-purple cone. Flowers and foliage are distinctively large. *Echinacea* is a popular genus, typically used as container plants or landscape plants.

4 Drawing Sheets

Latin name of the genus and species: *Echinacea purpurea.*
Variety denomination: 'ES18-20-01'.

BACKGROUND OF THE INVENTION

The new cultivar, *Echinacea* 'ES18-20-01', is the product of a planned breeding program by the inventor. The new variety was selected as a seedling from an open pollination program. The open-pollination resulting in the new variety was made during July of 2017 at a home nursery in Kempen, Germany. The seed parent is the unpatented proprietary variety of *Echinacea purpurea* referred to as 'ES17-02'. The pollen parent is unknown. The discovery was made during June of 2018, in Kempen, Germany, at the inventor's home nursery.

Asexual reproduction of the new cultivar 'ES18-20-01' was first performed in Kempen, Germany, at the same home nursery, by terminal vegetative cuttings n September of 2018. *Echinacea* 'ES18-20-01' has since produced at least three generations and has shown that the unique features of this cultivar are stable and reproduced true to type.

SUMMARY OF THE INVENTION

The cultivar 'ES18-20-01' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'ES18-20-01'. These characteristics in combination distinguish 'ES18-20-01' as a new and distinct *Echinacea* cultivar:

1. Ray florets typically colored Orange-Red 34B, heavily overlayed with Red 46B.
2. Dark greyed-purple cone color.
3. Larger flower than other red *Echinacea* varieties.
4. Large foliage.
5. Unique dark stem color near Greyed-Red 178A.

PARENTAL COMPARISON

Plants of the new cultivar 'ES18-20-01' are similar to plants of the parent in most horticultural characteristics. However, plants of the new cultivar 'ES18-20-01' differ in the following:

1. *Echinacea* 'ES18-20-01' has a darker ray floret color than the seed parent.
2. *Echinacea* 'ES18-20-01' has a larger flower diameter than the seed parent.
3. *Echinacea* 'ES18-20-01' has a less leggy plant habit than the seed parent.

COMMERCIAL COMPARISON

The new cultivar 'ES18-20-01' can be compared to the commercial variety *Echinacea* 'BALSOMSED', U.S. Plant Pat. No. 23,105. Plants of the new cultivar 'ES18-20-01' differ in the following:

1. *Echinacea* 'ES18-20-01' is lower growing than 'BALSOMSED', typically about 35 cm in height, compared to 42 cm of 'BALSOMSED' when grown under similar conditions.
2. *Echinacea* 'ES18-20-01' produces flowers with an average diameter around 8.9 cm, flower diameter of this comparator is about 7.5 cm.
3. Ray floret color of *Echinacea* 'ES18-20-01' is typically Orange-Red 34B, heavily overlayed with Red 46B. Typical ray floret color of this comparator is Red 45B.

The new cultivar 'ES18-20-01' can be compared to the unpatented *Echinacea* 'Mooodz Sympathy'. Plants of the new cultivar 'ES18-20-01' are similar to *Echinacea* 'Moodz Sympathy' in most horticultural characteristics. However, plants of the new cultivar 'ES18-20-01' differ in the following:

1. *Echinacea* 'ES18-20-01' produces flowers with an average diameter around 8.9 cm, flower diameter of this comparator is about 7.0 cm.
2. *Echinacea* 'ES18-20-01' produces larger foliage than this comparator.
3. *Echinacea* 'ES18-20-01' produces ray florets colored red-orange and red; ray florets of this comparator are more dark pink in color.

The new cultivar 'ES18-20-01' can be compared to the commercial variety *Echinacea* 'TNECHKRD', U.S. Plant Pat. No. 29,743. Plants of the new cultivar 'ES18-20-01' differ in the following:

1. *Echinacea* 'ES18-20-01' is lower growing than 'TNECHKRD', typically about 35 cm in height, compared to 47 cm of 'TNECHKRD' when grown under similar conditions.
2. Ray floret color of *Echinacea* 'ES18-20-01' is typically Orange-Red 34B, heavily overlayed with Red 46B. Typical ray floret color of this comparator is Red 46A blended with Greyed-Orange 170B.

The new cultivar 'ES18-20-01' can be compared to the commercial variety *Echinacea* 'BALSOMENCO', U.S. Plant Pat. No. 25,523. Plants of the new cultivar 'ES18-20-01' differ in the following:

1. *Echinacea* 'ES18-20-01' is lower growing than 'BALSOMENCO', typically about 35 cm in height, compared to 48 cm of 'BALSOMENCO' when grown under similar conditions.
2. *Echinacea* 'ES18-20-01' produces flowers with an average diameter around 8.9 cm, flower diameter of this comparator is about 7.5 cm.
3. Ray floret color of *Echinacea* 'ES18-20-01' is typically Orange-Red 34B, heavily overlayed with Red 46B. Typical ray floret color of this comparator is Orange 25A overlaid with Orange-Red, with a Red base.

BRIEF DESCRIPTION OF THE PHOTOGRAPHS

The photographs were taken using conventional techniques and equipment. While the colors in these photographs may display variances of color as compared to the living cultivar, due to LRV (light reflectance value), they are as accurate as possible using conventional photographic techniques. Colors in the photographs may appear to differ slightly from the color values cited in the botanical description, which accurately describe the colors of new *Echinacea* 'ES18-20-01'. Plants were grown in Kempen, Germany.

DETAILED BOTANICAL DESCRIPTION

Figure 1:
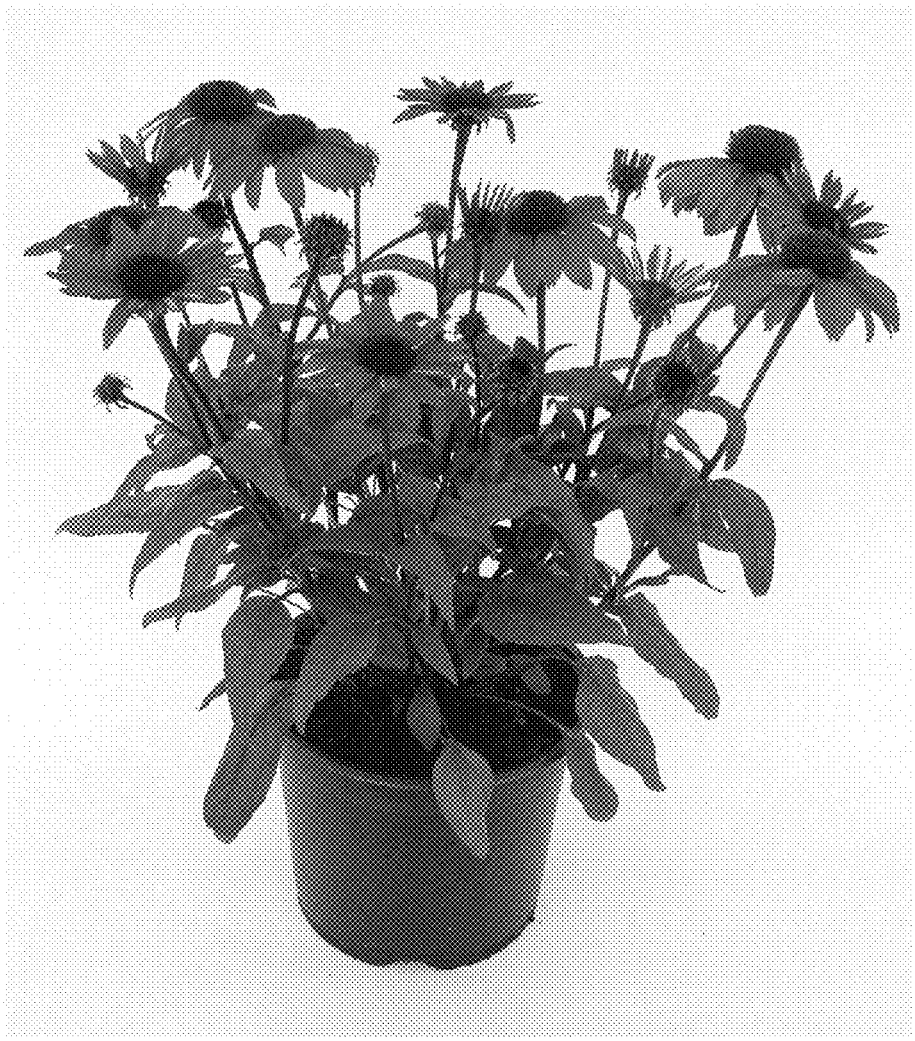
FIG. 1 illustrates in full color a plant of *Echinacea* 'ES18-20-01' grown in a 2 liter pot at approximately 1 year old.
Figure 2:
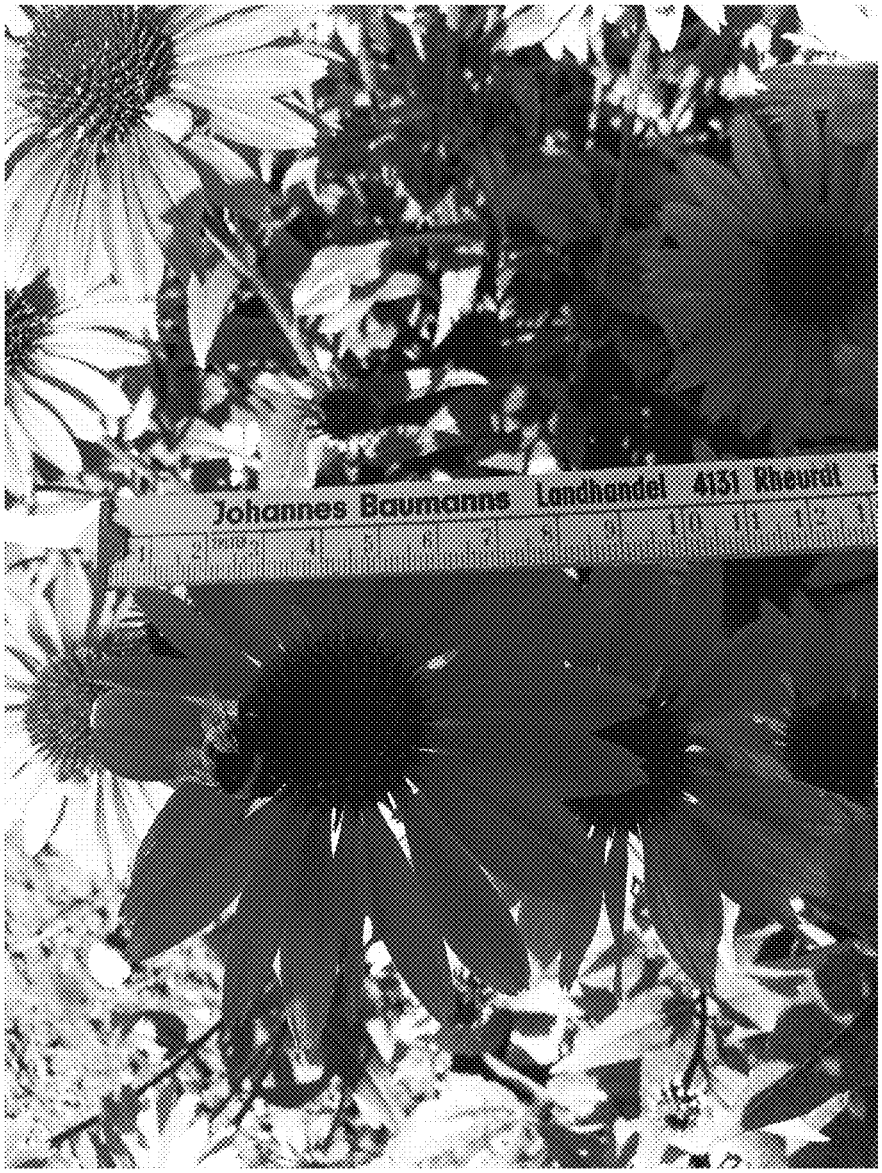
FIG. 2 illustrates in full color an inflorescence of *Echinacea* 'ES18-20-01', grown outdoors.
Figure 3:
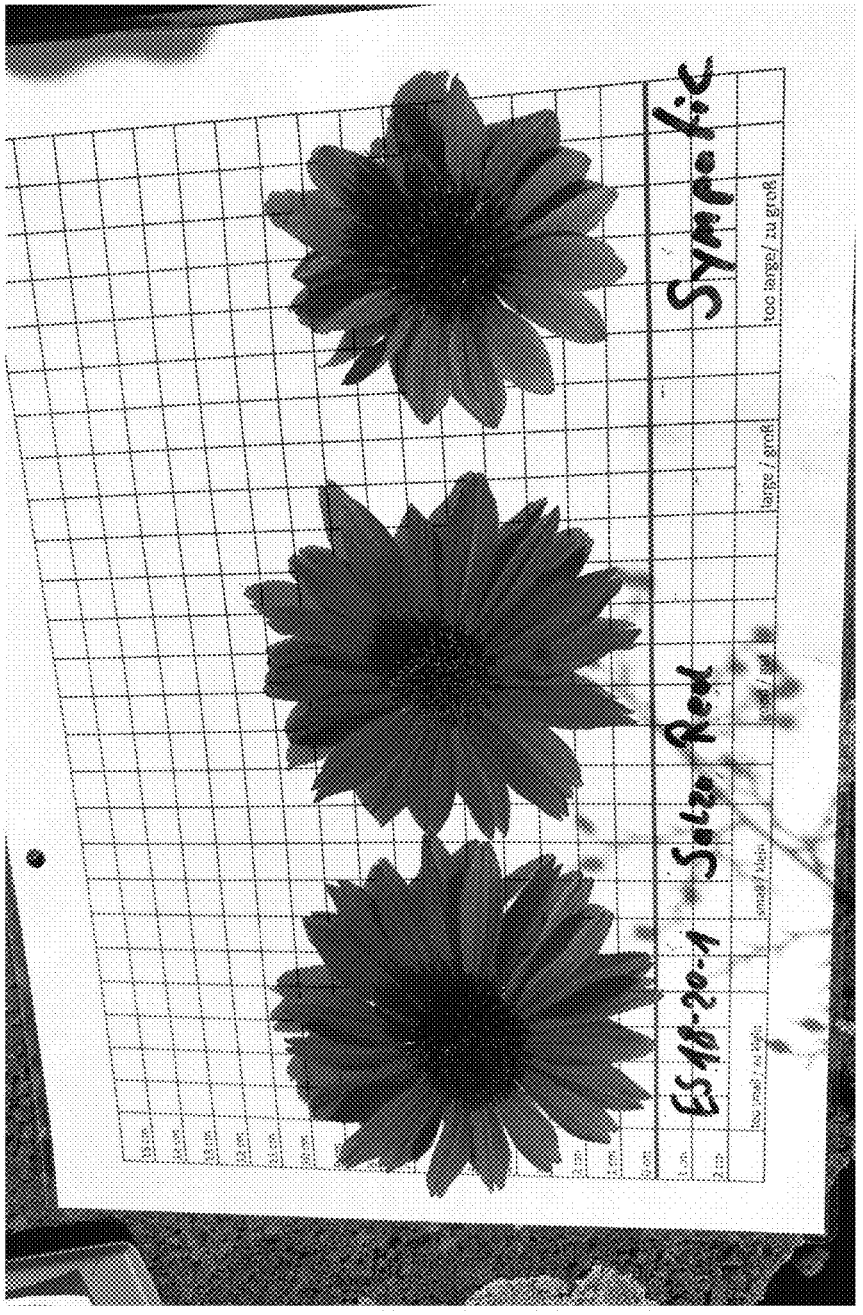
FIG. 3 illustrates in full color a comparison of the inflorescences of *Echinacea* 'ES18-20-01' (farthest left), *Echinacea* 'BALSOMSED' (center, commercially known in Europe as 'Salza Red'), and 'Mooodz Sympathy' (commercially known in Europe as 'Sympatic').
Figure 4:
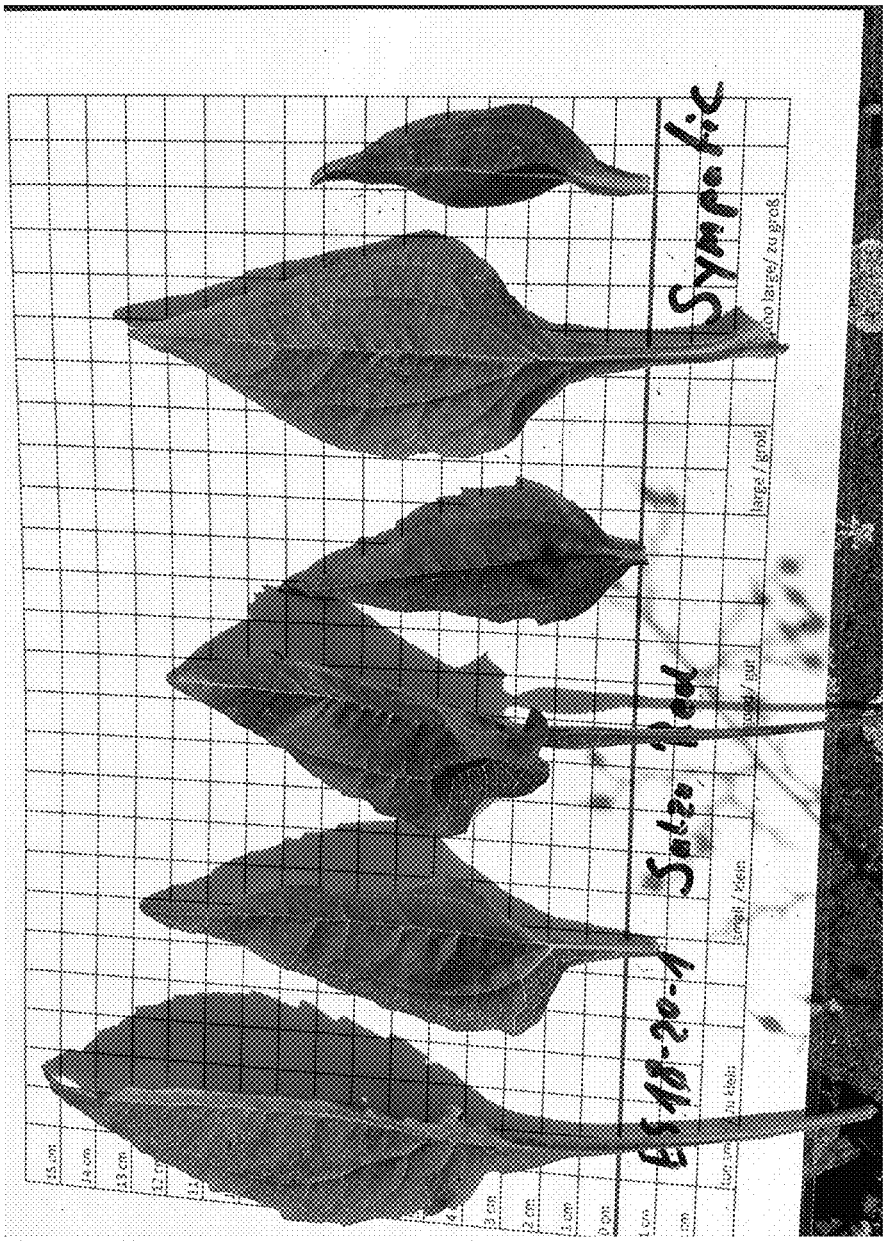
FIG. 4 illustrates in full color a comparison of the foliage of *Echinacea* 'ES18-20-01' (farthest left), *Echinacea* 'BALSOMSED' (center, commercially known in Europe as 'Salza Red'), and 'Mooodz Sympathy' (commercially known in Europe as 'Sympatic').

In the following description, color references are rrrade to The Royal Horticultural Society Colour Chart, 2007 except where general terms of ordinary dictionary significance are used. The following observations and measurements describe 'ES18-20-01' plants grown outdoors in High Hurstwood, United. Kingdom. Measurements and numerical values represent averages of typical plant types.

Botanical classification: *Echinacea purpurea* 'ES18-20-01'.

PROPAGATION

Time to rooting: 15 to 20 days at approximately 18° to 22° C.

Root description: Fibrous and branched. Young roots white, older roots creamy brown. Colors not accurately measured with RHS chart.

PLANT

Age of plant described: Approximately 12 months from a rooted cutting.

Growth habit: Hardy, upright, herbaceous perennial.

Height: Approximately 35 cm.

Plant spread: Approximately 45 cm.

Growth rate: Moderate.

Branching characteristics: Porrect, alternate.

Length of lateral branches: Approximately 7 cm.

Diameter of lateral branches: Approximately 0.2 cm.

Quantity of lateral branches: Approximately 3.

Texture of lateral branches: Hispid.

*Hair color.*—Near RHS White 155A.

Color of lateral branches: Near RHS Greyed-Red 178A.

Aspect: Approximately 15 to 20 degrees from vertical.

Internode length: Approximately 4.5 cm.

Number of leaves per lateral branch: Approximately 2.

FOLIAGE

Leaf:

*Arrangement.*—Alternate, simple. Average Length: Smallest apical leaves (blade), approximately 1.7 cm. Largest basal leaves (blade), approximately 9.0 cm. Average Width: Smallest apical leaves (blade) approximately 1.1 cm. Largest basal leaves (blade), approximately 5.9 cm. Shape of blade: Narrowly ovate to lanceolate. Apex: Acute. Base: Stem leaves attenuate, fused to stem; basal leaves — cordate to attenuate, fused to petiole. Attachment: Sessile, fused to stem in stem leaves, long petiole in basal leaves. Margin: Entire, widely serrate. Texture of top surface: Moderately hispid. Texture of bottom surface: Moderately hispid. Rugosity: Strong. Leaf internode length: Approximately 3.5 cm on stems. Basal leaves grow from ground level. Color: Young foliage upper side: Near RHS Yellow-Green 147A. Young foliage under side: Near RHS Yellow-Green 147B. Mature foliage upper side: Between RHS Green 137A and 137B. Mature foliage under side: Between RHS Green 137C and 137D. Venation: Type: Pinnate. Venation color upper side: Near RHS Yellow-Green 147D. Venation color under side: Near RHS Yellow-Green 144D.

Petiole: Basal leaves only.

*Length.*—Approximately 15 cm.

*Diameter.*—Approximately 0.2 cm.

*Texture.*—Glabrous near base, becoming sparsely pubescent near leaf blade.

*Shape.*—V-shaped in section.

*Color-upper side.*—Near RHS Green137B.

*Color-lower side.*—Near RHS 144D, faintly flushed with 183B.

FLOWER

Blooming period: Naturally blooming June to November (Kempen, Germany).

Bud:

*Bud shape.*—Oblate globular.

*Bud length.*—Approximately 0.9 cm.

*Bud diameter.*—Approximately 1.2 cm.

*Bud color.*—Near RHS Greyed-Purple 187A.

Inflorescence:

*Form.*—Composite, held terminally on strong peduncle, either singly or on a raceme bearing up to 3 flowers.

Flower:

*Diameter of entire flower.*—Approximately 8.9 cm.

*Depth of flower.*—Approximately 3.3 cm.

*Disc diameter.*—Approximately 2.4 cm.

*Disc height.*—3.3 cm.

*Disc type.*—Daisy.

*Receptacle shape.*—Conical.

*Receptacle height.*—Average 0.8 cm.

*Receptacle diameter.*—Average 1.4 cm.

*Quantity of open inflorescences and buds per plant.*—Average 8.

*Longevity.*—Approximately 20 days.

*Rate of opening.*—3 to 5 days from bud to fully opened flower.

*Persistent or self-cleaning.*—Persistent.

Ray Florets:

*Arrangement.*—Rotationally symmetric.

*Aspect/orientation.*—Perpendicular to disc, subtending with age in mature flower.

*Shape.*—Narrowly lanceolate to narrowly oblanceolate.

*Number of ray florets.*—Avg. 16.

*Length.*—Approximately 3.4 cm.

*Width.*—Approximately 1.2 cm.

*Apex shape.*—Incised with two acute tips.

*Base.*—Attenuate.

*Margin.*—Entire.

*Texture.*—Smooth, ribbed longitudinally.

*Twisting.*—Absent.

Color:

*Ray florets.*—Upper surface at first opening: Near RHS Red 44A with overlay Red 46B. Near 46A and 46B at base. Upper surface at maturity: Near RHS Orange-Red 34B, heavily overlaid 42A. Base Red 46B. Upper surface at fading: Near RHS Orange-Red N34B. Base Red 46B and 46C. Under surface at first opening: Near RHS Greyed-Purple 185B. Under surface at maturity: Near RHS Greyed-Purple 186A. Under surface at fading: Between Greyed-Purple 186B and 186C.

*Disc florets.*—Number of Disc Florets: Approximately 180. Arrangement: Spirally arranged in center of each inflorescence. Length: Approximately 0.8 cm. Width: Approximately 1.75 mm. Shape: Tubular. Margin: Entire. Apex: Five acute tips. Base: Fused into tube. Texture: Glabrous, glossy. Receptacle spines: Number of spines per disc floret: 1. Spine shape: Cylindrical with conical tips. Spine apex: Acute to attenuate. Spine texture: Glabrous, glossy. Spine apex color: Near RHS Greyed-Purple 183A. Spine mid-section color: Near RHS Red 46A. Spine base color: Near RHS Yellow-Green 147B.

*Disc florets Color.*—At first opening: Near RHS Yellow-Green 144C flushed with Greyed-Purple 183C. At maturity: Near RHS Greyed-Purple 187A.

Fragrance: Faint, sweet.

Phyllaries/involucral bracts.

*Arrangement.*—Three whorls.

*Number.*—Approximately 45.

*Length.*—Approximately 0.7 cm.

*Width.*—Approximately 0.25 cm.

*Shape.*—Narrowly ovate to lanceolate.

*Apex.*—Acute.

*Base.*—Truncate.

*Margin.*—Entire, hispid.

*Texture.*—Glabrous.

*Color.*—Adaxial surface color near RHS Yellow-Green 147B; 147A at margins. Abaxial surface color between Greyed-Purple 187A and 187B.

Peduncle:

*Length.*—Average 15 cm.

*Width.*—Average 0.35 cm.

*Texture.*—moderately hispid.

*Color.*—Between Greyed-Purple 187A and 187B.

REPRODUCTIVE ORGANS

Androecium:

*Stamens per disc floret.*—5.

*Filament length.*—Approximately 0.2 cm.

*Filament color.*—Near RHS Yellow-Green 145D.

*Anther shape.*—Oblong.

*Anther length.*—About 0.3 cm.

*Anther color.*—Near RHS Brown N200A.

*Pollen amount.*—Abundant.

*Pollen color.*—Near RHS Yellow 13B.

Gynoecium:

*Pistil length.*—Approximately 1 cm.

*Stigma shape.*—Decurrent.

*Stigma color.*—Near RHS Greyed-Purple 187A.

*Style length.*—About 0.5 cm.

*Style color.*—Near RHS Yellow-Green 145C.

*Ovary color.*—Near RHS Yellow-Green 145D.

OTHER CHARACTERISTICS

Fruits and seeds: Fertile, some seed set. Seeds achene, about 3 to 4 mm long and about 2 mm wide. Colored near Grey-Brown 199B.

Temperature tolerance: Hardy perennial to minus 20° C. Upper temperature tolerance to at least 45° C. (survived 8 days with 45° C. maximum in Summer 2020 at Kempen, Germany).

Disease/pest resistance: Neither resistance or susceptibility to normal diseases and pests of *Echinacea* has been observed.

Drought tolerance: Some drought tolerance, established plants can tolerate infrequent summer watering.

What is claimed is:

1. A new and distinct cultivar of *Echinacea* plant named 'ES18-20-01' as herein illustrated and described.

* * * * *